US010969385B2

(12) United States Patent
Mehra et al.

(10) Patent No.: US 10,969,385 B2
(45) Date of Patent: Apr. 6, 2021

(54) ROTORS FOR IMMUNOASSAYS

(71) Applicant: ZOETIS SERVICES LLC, Parsippany, NJ (US)

(72) Inventors: Rajesh K. Mehra, Union City, CA (US); Kenneth P. Aron, Union City, CA (US)

(73) Assignee: ZOETIS SERVICES LLC, Parsippany, NJ (US)

( * ) Notice: Subject to any disclaimer, the term of this patent is extended or adjusted under 35 U.S.C. 154(b) by 71 days.

(21) Appl. No.: 16/450,082

(22) Filed: Jun. 24, 2019

(65) Prior Publication Data
US 2019/0310246 A1 Oct. 10, 2019

Related U.S. Application Data

(60) Continuation of application No. 15/783,126, filed on Oct. 13, 2017, now Pat. No. 10,371,701, which is a
(Continued)

(51) Int. Cl.
*G01N 33/543* (2006.01)
*B01L 3/00* (2006.01)
(Continued)

(52) U.S. Cl.
CPC ...... *G01N 33/54366* (2013.01); *B01L 3/5023* (2013.01); *G01N 33/558* (2013.01); *G01N 33/581* (2013.01); *G01N 33/587* (2013.01); *B01L 2300/069* (2013.01); *B01L 2300/0681* (2013.01); *B01L 2300/0806* (2013.01);
(Continued)

(58) Field of Classification Search
CPC ........... G01N 33/54366; G01N 33/558; G01N 33/581; G01N 33/587; G01N 35/00069; B01L 3/5023; B01L 2300/0681; B01L 2300/069; B01L 2300/0806;
(Continued)

(56) References Cited

U.S. PATENT DOCUMENTS 4,313,734 A 2/1982 Leuvering
5,102,788 A 4/1992 Cole
(Continued)

FOREIGN PATENT DOCUMENTS

DE 102005016508 A1 10/2006
EP 0505636 A1 9/1992
(Continued)

OTHER PUBLICATIONS

Bui, et al., "Gold Nanoparticle Aggregation-Based Highly Sensitive DNA Detection Using Atomic Force Microscopy," Anal. Bioanal. Chem., vol. 388: 1185-1190, 2007.
(Continued)

*Primary Examiner* — Rebecca M Giere
*Assistant Examiner* — Christopher Q Lang
(74) *Attorney, Agent, or Firm* — Cooley LLP

(57) ABSTRACT

The present invention provides an analyte detection system for detecting target analytes in a sample. In particular, the invention provides a detection system in a rotor or disc format that utilizes a centrifugal force to move the sample through the detection system. Methods of using the rotor detection system to detect analytes in samples, particularly biological samples, and kits comprising the rotor detection system are also disclosed.

17 Claims, 2 Drawing Sheets

Related U.S. Application Data division of application No. 13/704,900, filed as application No. PCT/US2011/040878 on Jun. 17, 2011, now Pat. No. 9,816,987.

(60) Provisional application No. 61/355,847, filed on Jun. 17, 2010.

(51) Int. Cl.
*G01N 33/58* (2006.01)
*G01N 33/558* (2006.01)
*G01N 35/00* (2006.01)

(52) U.S. Cl.
CPC .......... *B01L 2300/0819* (2013.01); *B01L 2300/0864* (2013.01); *B01L 2400/0409* (2013.01); *G01N 35/00069* (2013.01)

(58) Field of Classification Search
CPC ..... B01L 2300/0819; B01L 2300/0864; B01L 2400/0409
USPC ........................................................ 436/518
See application file for complete search history.

(56) References Cited

U.S. PATENT DOCUMENTS

| | | | |
|---|---|---|---|
| 5,141,850 | A | 8/1992 | Cole et al. |
| 5,160,701 | A | 11/1992 | Brown et al. |
| 5,415,994 | A | 5/1995 | Imrich et al. |
| 5,451,504 | A | 9/1995 | Fitzpatrick et al. |
| 5,472,603 | A | 12/1995 | Schembri |
| 5,559,041 | A | 9/1996 | Kng et al. |
| 6,013,513 | A | 1/2000 | Reber et al. |
| 6,602,669 | B2 | 8/2003 | Letsinger et al. |
| 6,632,656 | B1 | 10/2003 | Thomas et al. |
| 7,189,368 | B2 | 3/2007 | Andersson et al. |
| 7,344,893 | B2 | 3/2008 | Kinkegaard et al. |
| 9,816,987 | B2 | 11/2017 | Mehra et al. |
| 10,371,701 | B2 | 8/2019 | Mehra et al. |
| 2002/0071362 | A1 | 6/2002 | Worthington |
| 2002/0074271 | A1 | 6/2002 | Hu et al. |
| 2002/0150503 | A1 | 10/2002 | Tanaka |
| 2003/0092090 | A1 | 5/2003 | Hajizadeh et al. |
| 2003/0096434 | A1 | 5/2003 | Krutzik |
| 2005/0026301 | A1 | 2/2005 | Petithory |
| 2005/0208593 | A1 | 9/2005 | Vail et al. |
| 2005/0249633 | A1 | 11/2005 | Blatt et al. |
| 2007/0042427 | A1 | 2/2007 | Gerdes et al. |
| 2007/0274863 | A1 | 11/2007 | Kido et al. |
| 2009/0035847 | A1 | 2/2009 | Cho et al. |
| 2010/0081213 | A1 | 4/2010 | Lee et al. |
| 2010/0136566 | A1 | 6/2010 | Mehra et al. |
| 2010/0255510 | A1 | 10/2010 | Wang et al. |
| 2013/0302830 | A1 | 11/2013 | Mehra et al. |
| 2018/0038853 | A1 | 2/2018 | Mehra et al. |

FOREIGN PATENT DOCUMENTS

| | | |
|---|---|---|
| EP | 1897617 A1 | 3/2008 |
| JP | 2006-349594 A | 12/2006 |
| WO | WO 1991/012336 A1 | 8/1991 |
| WO | WO 1988/008534 A1 | 11/1991 |
| WO | WO 2000/058724 A1 | 10/2000 |
| WO | WO 2002/004681 A2 | 1/2002 |
| WO | WO 2006/060922 A2 | 6/2006 |
| WO | WO 2006/118420 A1 | 11/2006 |
| WO | WO 2008/086054 A2 | 7/2008 |

OTHER PUBLICATIONS

Chan, et al., "New Trends in Immunoassays," Adv Biochem Eng Biotechnol., vol. 109:123-154, 2008.
Extended European Search Report for European Patent Application No. 11796504.6, dated Oct. 4, 2013, 10 pages.
Gupta, et al., "Characterization and Optimization of Gold Nanopaiiicle-Based Silver-Enhanced Immunoassays," Anal. Chem., vol. 79(10):3810-3820, 2007.
International Preliminary Report on Patentability for International Patent Application No. PCT/US2011/040878, dated Dec. 19, 2012, 4 pages.
International Search Report and Written Opinion for International Patent Application No. PCT/US2011/040878, dated Feb. 29, 2012, 6 pages.
Laderman, et al., "Rapid, Sensitive, and Specific Lateral-Flow immunochromatographic Point-of-Care Device for Detection of Herpes Simplex Virus Type 2—Specific Immunoglobulin G Antibodies in Serum and Whole Blood," Clin. Vaccine Immunol., vol. 15(1): 159-163, 2008.
Nitin, et al., "Oligonucleotide-Coated Metallic Nanoparticles as a Flexible Platform for Molecular Imaging Agents," Bioconjug. Chem., vol. 18(6):2090-2096, 2007.

ROTORS FOR IMMUNOASSAYS

CROSS-REFERENCE TO RELATED APPLICATIONS

This application is a Continuation application to U.S. patent application Ser. No. 15/783,126, filed Oct. 13, 2017, which is a Divisional application to U.S. patent application Ser. No. 13/704,900, filed Feb. 21, 2013 (now U.S. Pat. No. 9,816,987, issued Nov. 14, 2017), which is the U.S. national stage application to International Patent Application No.: PCT/US2011/040878, filed Jun. 17, 2011, which claims priority to U.S. Provisional Application No. 61/355,847, filed Jun. 17, 2010, which are herein incorporated by reference in their entireties.

FIELD OF THE INVENTION

The present invention relates to an analyte detection system for detecting a target analyte in a sample, e.g. a biological sample. In particular, the present invention provides a detection system in a rotor format that utilizes a centrifugal force to move the sample through the detection system.

BACKGROUND OF THE INVENTION

One of the most common types of assays used as a rapid point of care test to detect a particular analyte in a biological sample is a lateral flow strip-based assay. Such assays typically contain a binding partner for the analyte of interest coupled to a detectable label (i.e. labeled conjugates) and a porous membrane on which a capture protein (e.g. antibody or antigen) capable of binding the analyte of interest is immobilized. Labeled conjugates that are commonly used in these types of assays are antibodies or antigens coupled to gold nanoparticles or colored latex particles. An analyte present in the sample will bind to the labeled conjugate to form a complex. The complex continues to migrate through the porous membrane to the region where the capture protein is immobilized at which point the complex of analyte and labeled conjugate will bind to the capture protein. The presence of the analyte is then determined by detecting the labeled conjugate in the capture region of the porous membrane (e.g. by a color change of the capture line).

Although lateral flow strip-based assays have proven useful for rapid detection of sonic analytes in the clinical setting, such assays suffer from several disadvantages. For example, lateral flow strip-based assays require a series of overlapping porous materials to achieve efficient sample flow through the device. Construction of such devices can be cumbersome and somewhat costly depending on the porous materials that are employed. Also, lateral-strip based assays are inherently limited by their sensitivity due to the occurrence of a single binding event and are often limited to a qualitative analysis. In addition, detection of multiple analytes in a single sample simultaneously is often difficult to achieve with conventional lateral flow strip-based assays.

Thus, there is a need in the art to develop novel devices and methods for the detection of multiple analytes in a sample, particularly a biological sample, which can provide quantitative results as well as qualitative results.

SUMMARY OF THE INVENTION

The present invention is based, in part, on the discovery that a centrifugal force can be used to direct fluid sample through radial flow paths such that the fluid sample contacts reagents and immobilized binding partners positioned within the flow paths. A detection device employing radial flow paths obviates the need to use the overlapping porous surfaces of conventional lateral flow devices to achieve proper sample flow through the device. In addition, such devices can contain multiple radial flow paths and thus the presence of multiple analytes can be detected simultaneously in a single sample. Accordingly, the present invention provides an analyte detection system in a rotor or disc format that allows for the detection of multiple analytes in a biological sample.

In one embodiment, the detection system comprises a centrifugal force, a sample port and a surface, wherein the surface comprises at least one channel, said channel containing an immobilized capture ligand capable of specifically binding to an analyte in a sample, wherein the sample port is in fluid communication with said at least one channel, and wherein the centrifugal force is operably connected to the sample port so that when in operation it causes a sample deposited in the sample port to move through the at least one channel and be in fluid contact with the capture ligand. In some embodiments, the one or more channels can be part of a flow path allowing the sample to flow radially outward when a centrifugal force is applied to the system. In other embodiments, the one or more channels can be part of a flow path allowing the sample to flow along a circular path when a centrifugal force is applied to the system. In another embodiment, the surface further contains at least one absorbing entity located downstream from the capture ligand.

In some embodiments, the channel further contains a conjugate capable of binding to the analyte in the sample to form a complex, wherein the complex is captured by the capture ligand. Conjugates present in the one or more channels of the surface can comprise a binding partner conjugated to a detectable entity, wherein the binding partner is capable at specifically binding to a target analyte in a sample. In some embodiments, the binding partner is an antibody or antigen. The detectable entity can be a metal particle (e.g. metal nano-particle or metal nanoshell), fluorescent molecule, colored latex particle, or an enzyme. In one embodiment, the detectable entity is a gold nanoparticle.

In another embodiment, the channel comprises a first flow path and a second flow path, wherein said first and second flow paths are positioned in different planes, and wherein said first and second flow paths are in fluid communication. The first flow path can comprise an immobilized capture ligand and a conjugate capable of binding to an analyte in a sample to form a complex that can be captured by the capture ligand. The second flow path can comprise a substrate region, which comprises a substrate entity capable of interacting with the detectable entity of the conjugate to produce or amplify a detectable signal. In one embodiment, the first flow path provides a faster flow through than the second flow path when a centrifugal force is applied to the channel In certain embodiments, the surface of the detection system comprises a plurality of channels (e.g., two or more channels), wherein each said channel comprises an immobilized capture ligand capable of specifically binding to an analyte in a sample. In one particular embodiment, each channel further comprises a conjugate capable of binding to an analyte the sample to form a complex and wherein the complex is captured by a capture ligand. In some embodiments, each conjugate specifically binds to a different target analyte in a sample. In one embodiment, each of the channels comprises a first and second flow path, wherein said first and second flow paths are located in different planes and are in fluid communication.

In another embodiment, the sample port of the detection system comprises one or more conjugates capable of binding to an analyte in the sample to form a complex, wherein the complex is captured by a capture ligand. The conjugates can bind different analytes the sample and may, in some embodiments, contain different detectable entities. In certain embodiments, the surface of the detection system contains a channel, wherein the channel comprises a first capture ligand and a second capture ligand, wherein the first capture ligand is located upstream from the second capture ligand. In one embodiment, the first capture ligand specifically binds a different analyte than the second capture ligand.

In some embodiments, the one or more channels of the detection system further contain a positive or negative control entity. The control entity can comprise a control binding partner that binds to the conjugate (e.g. binding partner or detectable entity). A detection signal from the control entity can indicate proper fluid flow through the detection system.

The present invention also provides a kit comprising an analyte detection system of the invention and instructions for using the system to detect one or more target analytes in a sample. The detection systems are adapted for use with a centrifugal force and in some embodiments, can be used with conventional centrifuges with appropriate attachments. The kit can further comprise means for collecting samples and buffers for extracting samples from solid substances.

The present invention includes a method for detecting an analyte in a sample. In one embodiment, the method comprises adding the sample to the sample port of an analyte detection system of the invention, applying a centrifugal force to the system, and detecting the binding of the analyte to the capture ligand. The sample can be a biological sample isolated from a human or animal subject in some embodiments, multiple (e.g., two or more) analytes are detected from a single sample simultaneously.

DETAILED DESCRIPTION OF THE INVENTION

Figure 1:
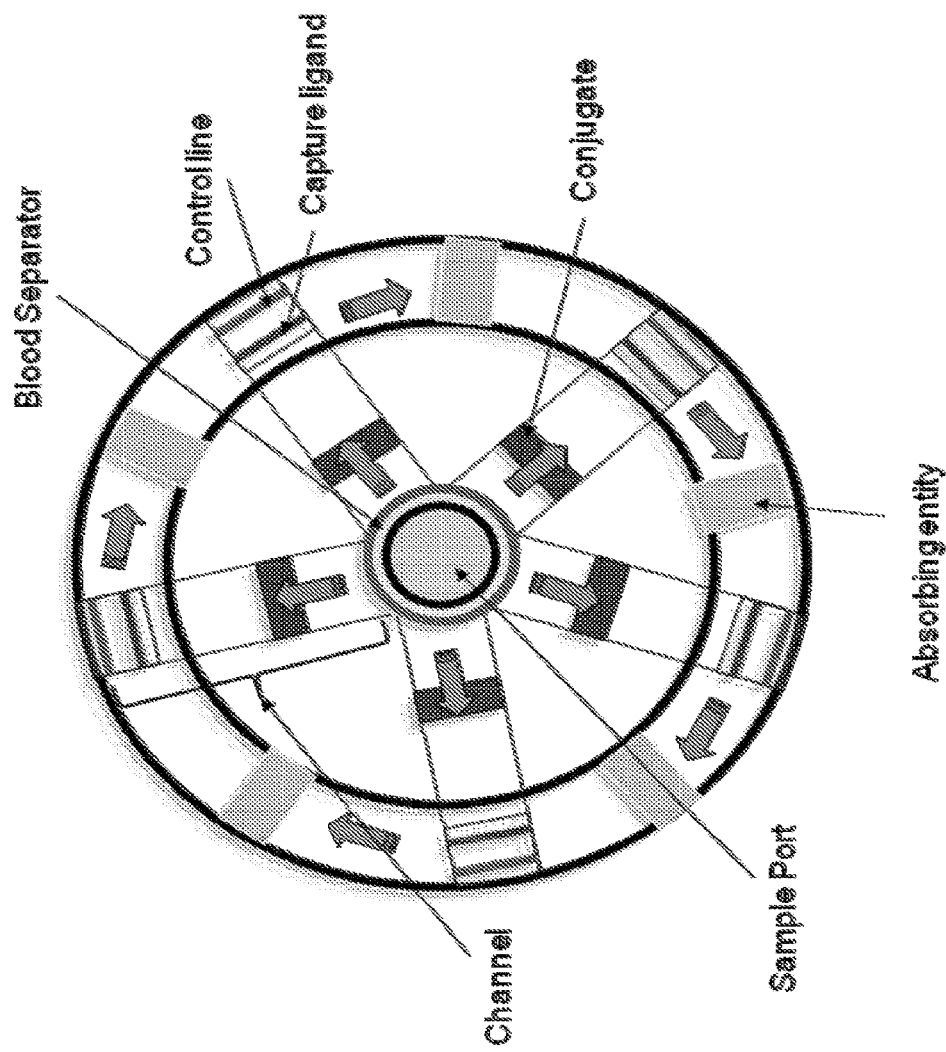
FIG. 1 depicts a top view of one embodiment of the analyte detection system of the present invention. A surface (e.g. rotor base or disc) contains a plurality of channels that are in fluid communication with a sample port. Each channel contains a conjugate comprised of a binding partner conjugated to a detectable entity that can specifically bind to a target analyte present in the sample. At the peripheral edge of each channel is a capture ligand capable of binding the analyte-conjugate complex. The peripheral edge of each channel can optionally contain a control line that indicates sufficient fluid flow through the system. When a centrifugal force is applied to the surface and sample port, a fluid sample deposited in the sample port flows radially through the channels to the periphery of the surface (Hue arrows), and excess fluid is absorbed by absorbent material (absorbing entity) positioned downstream of each capture ligand. The surface can optionally contain a blood separator material, which allows plasma from a blood sample to pass into the system while retaining cellular material in the sample port.

The present invention is based, in part, on the discovery that multiple analytes in a sample can be detected simultaneously by utilizing a centrifugal force to direct a fluid sample through multiple radial flow paths, Accordingly, the present invention provides an analyte detection system in a rotor or disc format that can provide qualitative or quantitative detection of a range of analytes in test samples.

In one embodiment, the analyte detection system comprises a centrifugal force, a sample port, and a surface, wherein the surface comprises at least one channel, said channel containing an immobilized capture ligand capable of specifically binding to an analyte in a sample, wherein the sample port is in fluid communication with said at least one channel, and wherein the centrifugal force is operably connected to the sample port so that when in operation it causes a sample deposited in the sample port to move through the at least one channel and be in fluid contact with the capture ligand.

The surface is preferably a disc (e.g. circular) or rotor shape and contains at least one channel In some embodiments, the surface contains a plurality of channels, for instance, two or more, three or more, four or more, five or more, six or more, seven or more, eight or more, nine or more, or ten or more channels The number of channels on the surface can be adjusted to accommodate the number of analytes that are to be detected simultaneously. The total number of channels is limited only by the area of the surface, which in turn is limited by dimensions of conventional centrifuges. In certain embodiments, the surface is proportioned to fit within conventional centrifuges.

The surface can be constructed of a wide variety of materials, including but not limited to, plastic, acrylic resin, silica plate, metal plate, polycarbonate, polypropylene, ceramic material, or a laminated or coated material. The surface should be constructed of a material that is able to withstand a centrifugal force of at least 1,600 g. One or more channels can be formed in the surface material by creating depressions using conventional techniques. Alternatively, the channels can be formed by affixing pre-formed channels (e.g. plastic strips) to the surface. The channels are preferably arranged radially on the surface such that the channels provide a flow path from the sample port, which can be located at the center of the surface, to the peripheral edge of the surface. For instance, in one embodiment, the one or more channels are part of one or more flow paths that allow the sample to flow radially outward when a centrifugal force is applied to the sample port and surface (see, e.g., FIG. 1). In another embodiment, the surface comprises a single channel that is part of a flow path allowing the sample to flow along a circular path (e.g. around the circumference of the surface) when a centrifugal force is applied to the sample port and surface (see, e.g., FIG. 2).

The sample port is in fluid communication with one or more channels present on the surface. As used herein, "fluid communication" refers to the ability of a liquid to flow or travel between two materials or surfaces. Fluid communication can be established between two porous materials or between a porous material and anon-porous material. In the latter situation, the non-porous material can form a channel or conduit by which fluid can flow by capillary action to establish fluid communication between the non-porous material and the porous material. In some embodiments, sample deposited in the sample port flows into one or more channels forming a flow path from the center of the surface to the periphery or outer edge of the surface.

In certain embodiments, the sample port is positioned at the center of the surface. The sample port provides an entry point for liquid sample to be applied to the detection system. As discussed in more detail below, liquid sample applied to the sample port can enter one or more radial flow paths when a centrifugal force is applied to the sample port. In some embodiments, the sample port comprises a sample reagent selected from the group consisting of blocking agents, neutralizing agents, buffers, detergents, antimicrobials, and combinations thereof. One or more of the sample reagents may be dried into a pad positioned in the sample port. The pad can be manufactured from one of several materials, including but not limited to, polyester, polyacrylic, other polymeric materials, or glass fiber.

In one embodiment, the sample port comprises a blocking agent. A "blocking agent" is an agent that prevents the non-specific association of proteins present in the sample with the conjugates, the immobilized capture ligands, and/or target analytes. Blocking agents are typically proteins themselves and can include, but are not limited to, bovine serum albumin, casein, gelatin, ovalbumin, gamma-globulins, and IgG from non-immunized animals. In another embodiment, the sample port comprises a neutralizing agent. A "neutralizing agent" is an agent that reduces the chemical reactivity of at least one interfering species. An interfering species can be a biological molecule or other compound present in a sample that exhibits anon-specific binding affinity to the detectable entity in the conjugate, Non-limiting examples of neutralizing agents include alkylating agents, such as iodoacetamide, iodoacetate, N-ethylmaleimide, PEG-maleimide, ethly-methanesulfonate, 4-vinylpyridine, nitrogen mustards, nitrosourea compounds, dacarbazine, and temozolomide. Neutralizing agents are described in detail in WO 2010/006201, filed Jul. 9, 2009, which is herein incorporated by reference in its entirety.

The sample port can comprise other various sample reagents including, but not limited to, buffers for maintaining the pH of the sample, detergents to enhance fluid flow, accelerants for enhancing the rate of immunoreactions, and antimicrobials to prevent biological contamination. Non-limiting examples of suitable buffers include iris, Hepes, imidazole, phosphate and other standard buffers typically used in lateral flow assays. Suitable detergents that may be used include, but are not limited to, Tween-20, Triton X-100, saponin, zwittergents based on sulfobetaines, CHAPS, octyl glucosides, and lauryl sulfates. Suitable accelerants that may be incorporated into the sample port include, but are not limited to, polyethylene glycols, polyvinyl alcohols, and polyvinylpyrrolidones. Exemplary antimicrobials that may be incorporated into the sample port include sodium azide, thimerosal, Proctins, antibiotics (e g Aminoglycosides, Ansaniycins, Carbacephem, Carbapenems, Cephalosporins, Macrolides, Monobactams, Penicillins, Quinolones, Sulfonamides, and Tetracyclines), antivirals (e.g. amantadine, rimantadine, pleconaril, acyclovir, zanamivir, and oseltamivir), antifungals (e.g. Natamycin, Rimocidin, Filipin, Nystatin, Amphotericin B, Candicin. Imidazoles, Triazoles, Allylamines, and Echinocandins), and antiparasitics (e.g. Mebendazole, Pyrantel pamoate, Thiabendazole, Diethycarbazine, Niclosamide, Praziquantel, Rifampin, Amphotericin B, and Melarsoprol), One of ordinary skill in the art can select other appropriate antimicrobials, buffers, accelerants, and detergents based on the particular sample type to be screened and the particular target analytes to be assayed without undue experimentation.

In certain embodiments, the sample port comprises a blood separator material. A blood separator material can be a filter material with pore sizes that allow plasma in a whole blood sample to pass through the filter and enter the detection system while cells and cellular debris are retained on the filter. For instance, filter materials with a micron rating of 8 pm or lower may be used. Blood separating materials are available commercially from Pall (Vivid), MDI (FR1 and FR2) and Whatman (Fusion 5).

In some embodiments, the one or more channels present on the surface contain an immobilized capture ligand. The capture ligand is capable of specifically binding to a target analyte in a sample. The capture ligand can be a biological macromolecule, such as an antibody or a region thereof (e.g., Fv, single chain, CDR, antibody expressed in phage display, etc.), a receptor, a ligand, a polynucleotide, an aptamer, a polypeptide, a polysaccharide, a lipopolysaccharide, a glycopeptide, a lipoprotein, or a nucleoprotein. In some embodiments whole cells, bacteria, or viruses can be immobilized to serve as the capture ligands. The capture ligand can be the same type of molecule as the binding partner in the conjugate, but preferably interacts with the target analyte at a location distinct from that as the binding partner. By way of example, the binding partner and the capture ligand can both be antibodies that recognize a target analyte, but the epitope to which the binding partner binds the target analyte is separate from the epitope to which the capture ligand binds the target analyte.

In one particular embodiment, the capture ligand is immobilized in the channel at a point downstream of the sample port. As used herein, "downstream" refers to the direction of fluid flow toward the end of the detection system and away from the site of sample application. In some embodiments, downstream refers to fluid flow radially outward from the center of the surface to the peripheral edge of the surface. "Upstream" refers to the direction of fluid flow away from the end of the detection system and toward the site of sample application. In some embodiments, the surface comprises a plurality of channels, said channels each comprising an immobilized capture ligand capable of specifically binding to an analyte in a sample. See, e.g., FIG. 1. Each capture ligand can specifically bind to a different analyte in the sample such that one detection system can be used to simultaneously detect multiple analytes present in a single sample. Thus, each radial flow path formed by each channel can contain an immobilized capture ligand capable of binding specifically to a particular analyte in a sample, In other embodiments, different capture ligands can be immobilized at different points on the peripheral edge of the surface. See, FIG. 2. For instance, the surface can comprise a single channel that contains a first capture ligand and a second capture ligand, wherein the first capture ligand is located upstream from the second capture ligand. In some embodiments, the surface can comprise a plurality of capture ligands arranged sequentially along the sample flow path. In such embodiments, the channel can form part of a flow path allowing the sample to flow along a circular path (e.g. around the circumference of the surface) when a centrifugal force is applied to the sample port and surface. In one embodiment, the capture ligands are capable of specifically binding different target analytes present in the sample. By way of example, the first capture ligand is capable of specifically binding a first target analyte and the second capture ligand is capable of specifically binding a second target analyte. In another embodiment, the different sets of capture ligands are capable of specifically binding the same target analyte and each set of capture ligands reflects a particular concentration at analyte. For instance, a first capture ligand can he Immobilized at a low concentration, a second capture ligand can be immobilized at a medium concentration, and a third capture ligand can be immobilized at a high concentration. A sample containing a medium concentration of the target analyte will contact and bind the first capture ligand. Having saturated the first capture ligand, excess target analyte will flow to and bind the second capture ligand. Since the target analyte in the sample will have bound to either the first or second capture ligand, no target analyte remains to flow to and bind the third capture ligand. Thus, the device will give a read out at the first and second capture ligands, but not the third capture ligand. The concentration of the target analyte in the sample can then be calculated based on the binding of the analyte at the different sets of capture ligands.

The capture ligands can be immobilized directly to the surface material or channel material. Alternatively, the capture ligands can be immobilized to a porous material, which in turn is affixed to the surface or channel material, A "porous" material refers to a material containing a plurality of interstices or pores through which liquid easily flows. The porous material can be made from natural or synthetic substances. Suitable porous materials for use in the detection system of the present invention include, but are not limited to, nitrocellulosic material, acrylic material, PVDF, polyethylene material (e.g. Porex®), nylon, cellulose acetate, polyester material, PES material, or polysulfone material. Other appropriate porous materials that can be used in the detection systems of the invention are known to those skilled in the art. The capture ligands can be immobilized to various materials (e.g. porous materials) by a variety of procedures. The capture ligands can be striped, deposited, or printed on the material followed by drying of the surface to facilitate immobilization. Immobilization of the capture ligands can take place through adsorption or covalent bonding. Depending on the nature of the material (e.g. type of material), methods of derivatization to facilitate the formation of covalent bonds between the material and the capture ligand can be used. Methods of derivatization can include treating the material with a compound, such as glutaraldehyde or carbodiimide and applying the capture ligand. Other physical, chemical, or biological methods of immobilizing a macromolecule or other substance either directly or indirectly to a material are known in the art and can be used to immobilize the capture ligand to the surface material, channel material, or porous material of the detection system. In embodiments which utilize porous materials, the porous material on which the capture ligand is immobilized may be treated with a blocking agent, sun as bovine serum albumin or other blocking agent as described herein.

In certain embodiments, the one or more channels present on the surface further comprise a conjugate capable of binding to the analyte in the sample to form a complex, wherein the complex is captured by the capture ligand. The conjugate comprises a binding partner conjugated or linked to a detectable entity. The binding partner can be any entity that is capable of specifically binding to a target analyte. In some embodiments, the binding partner is a biological macromolecule, including but not limited to an antibody or a region thereof (e.g., Fv, single chain, CDR, antibody expressed in phage display, etc.), a receptor, a ligand, a polynucleotide, an aptamer, a polypeptide, a polysaccharide, a lipopolysaccharide, a glycopeptide, a lipoprotein, or a nucleoprotein. In one embodiment, the binding partner is an antibody. In another embodiment, the binding partner is an antigen.

As used herein, "detectable entity" is an entity that is capable of producing a detectable signal under a particular set of conditions. In one embodiment, the detectable entity is an entity that exhibits wavelength selective absorption in the ultra-violet, visible, or near infrared electromagnetic spectrum and scatters incident radiation. For instance, the detectable entity can be a metallic nanoparticle or metallic nanoshell, Various types of metallic nanoparticles that can be coupled to the binding partner include, but are not limited to, gold nanoparticles, silver nanoparticles, copper nanoparticles, platinum nanoparticles, cadmium nanoparticles, composite nanoparticles (e.g. silver and gold or copper and silver), and gold hollow spheres. In some embodiments, the detectable entity is a gold nanoparticle. Additionally, metal nanoshells as described in U.S. Pat. No. 6,699,724, which is herein incorporated by reference in its entirety, can also be used as the detectable entity. Metal nanoshells are particles comprised of a dielectric core and a metallic coating that have a defined core radius to shell thickness ratio. The core can be comprised of a variety of materials including silicon dioxide, gold sulfide, titanium dioxide, and polystyrene. Suitable metals for the shell include gold, silver, copper, platinum, palladium, lead, and iron. Gold-coated silica nanoshells or silica-coated gold shells are preferred in some embodiments, In some embodiments, the detectable entity is an enzyme. Preferably the enzyme is capable of converting a substrate into a detectable product, e.g., colored, fluorescent, or chemiluminescent product. Non-limiting examples of enzymes that are suitable for conjugation to the binding partner include alkaline phosphatase, horseradish peroxidase, beta-galactosidase, beta-lactamase, galactose oxidase, lactoperoxidase, myeloperoxidase, and amylase. In another embodiment, the detectable entity is a metallic nanoparticle conjugated to an enzyme.

Other molecules, such as fluorescent molecules (e.g. fluorescein, Texas-Red, green fluorescent protein, yellow fluorescent protein, cyan fluorescent protein, Alexa dye molecules, etc.), that are known to those skilled in the art can be used as detectable entities in the conjugates of the invention. In some embodiments, the detectable entity is a colored latex particle as described, for example, in U.S. Pat. No. 4,837,168, which is herein incorporated by reference. In one embodiment, the conjugate is an antibody-nanoparticie conjugate. In another embodiment, the conjugate is an antibody-colored latex particle conjugate. In another embodiment, the conjugate is an antigen-nanoparticle conjugate. In still another embodiment, the conjugate is an antibody-enzyme conjugate. In yet another embodiment, the conjugate is an antibody-enzyme-nanoparticie conjugate. The enzyme in such conjugates can be alkaline phosphatase, horse radish peroxidase, or β-galactosidase.

Methods of conjugating a detectable entity (e.g. metallic nanoparticles, metallic nanoshells, colored latex particles, fluorescent molecules, and enzymes) to a binding partner are well known in the art. One such method for coupling a metallic nanoparticle or metallic nanoshell to a binding partner is by passive adsorption. This method involves adjusting the pH of the metal colloid solution to a pH at which the protein or other binding partner to be labeled has a positive charge, mixing the metal colloid solution with the binding partner solution, and centrifuging the resultant mixture. The labeled binding partner (e.g. protein) is then obtained by removing the supernatant and resuspending the precipitate. Other methods of conjugating macromolecules to detectable entities are known to the skilled artisan, who can select the proper method based on the type of desired detectable entity to be used and the type of macromolecule to be labeled. In some embodiments, the binding partner can be coupled to the detectable entity indirectly through a larger carrier molecule or protein. Such indirect coupling is particularly useful when the binding partner is small, such as a hormone, drug, or other small molecule less than 10 kD. For example, the detectable entity (e.g., gold nanoparticle) coupled to streptavidin can be conjugated to biotinylated binding partners (e.g., antigens or antibodies). Preferably, the carrier protein is not capable of specific interaction with the target analyte. In some embodiments, the binding partner is coupled to the detectable entity to form the conjugate prior to deposition of the conjugate on the surface or channel material.

In certain embodiments, the one or more channels present on the surface comprise a first flow path and a second flow path. Preferably, the first and second flow paths are located in different planes and are in fluid communication. For instance, the first flow path of the channel can be located in a top plane, while the second flow path of the channel can be located in a bottom plane positioned directly underneath the top plane. Thus, fluid flow through such a channel will be split into two flow paths when a centrifugal force is applied to the system. Devices with similar split flow paths are described in PCT/US2010/026948, filed Mar. 11, 2010, which is herein incorporated by reference in its entirety. The dual flow paths allow for easy amplification of the detection signal without the need for multiple reagent application steps or washes. In one embodiment, the first flow path provides a faster flow through than the second flow path when a centrifugal force is applied to the one or more channels. For instance, in some embodiments, the fluid flow through the first and second flow paths is controlled by employing different materials (e.g., different porosity membranes, presence of detergents) in the two flow paths or altering the lengths of each of the flow paths. In other embodiments, the fluid flow through the first and second flow paths is controlled by applying different, sequential centrifugal forces to the flow paths i.e. employing a lower speed spin followed by a higher speed spin to the detection system. In still other embodiments, the first and second flow paths may contain different materials such that fluid flow through the second flow path is slower than fluid flow through the first flow path. Combinations of different materials in the two flow paths and sequential application of increasing centrifugal forces to the detection system to achieve different flow rates through the first and second flow paths are also contemplated.

In one embodiment, the first flow path comprises an immobilized capture ligand and a conjugate capable of binding to an analyte in the sample as described herein. In another embodiment, the conjugate is positioned upstream of the capture ligand. In some embodiments, the first flow path is in fluid communication with the sample port such that liquid sample deposited in the sample port will flow into the first flow path when a centrifugal force is applied to the system.

In another aspect of the invention, the second How path comprises a substrate region. The substrate region can contain a pad in which one or more substrate entities (e.g. enzyme substrates, amplifying reagents, polymers, etc.) are dried. In some embodiments of the invention, the conjugate located in the first flow path comprises a binding partner conjugated to a detectable entity and the substrate region comprises a substrate entity capable of interacting with the detectable entity to produce a detectable signal. By way of illustration, if the conjugate comprises an enzyme as the detectable entity, the substrate region can comprise a substrate for that enzyme wherein a colored, fluorescent, or chemiluminescent substance is produced from the substrate after reaction with the enzyme. The specific substrate will depend upon the type of enzyme used as the detectable entity and the type of signal desired (e.g. color change or fluorescent signal). Some examples of suitable substrates include, but are not limited to, 2,2'-Azino-bis-(3-ethylbenziazoline-6-suifortic acid) (ABTS), 3-Amino-9-ethylcarbazoie (AEC), 5-bromo-4-chloro-3-indolyl phosphate/tetranitroblue tetrazolium chloride (BCIP/NBT), 5-bromo-4-chloro-3-indolyl phosphate/tetranitroblue tetrazolium (BCIP/TNBT), lumiphos®, 3,3'-Diaminobenzidine (DAB), 3,3',5,5'-Tetramethylbenzidine (TMB), 5-bromo-4-chloro-3-indolyl-beta-D-galactopyranoside (X-Gal), phosphastes indoxyls substituted at various positions in combination with a variety of tetrazolium dyes, naphthol phosphates in combination with Fast dyes, 4-CN, cobalt-DAB, and Gold-DAB, Various chromogenic, fluorogenic, and chemiluminescent substrates are commercially available for standard enzymes, such as alkaline phosphatase and horseradish peroxidase. Such commercially available enzyme substrates can be used in the detection system of the invention.

In other embodiments of the invention, the conjugate in the first flow path comprises a binding partner conjugated to a detectable entity and the substrate region comprises a substrate entity capable of interacting with the detectable entity to amplify the signal from the detectable entity. For instance, in one embodiment, the detectable entity is a gold nanoparticle and the substrate entity is silver nitrate. In another embodiment, the detectable entity is a metallic nano-particle and the substrate entity is 3,3',5,5'-Tetramethylbenzidine (FMB) or an indigo-containing product. The substrate region may comprise one or more amplifying reagents that intensify the signal from the detectable entity (e.g. metal nanoparticles or metal nanoshells). Such amplifying reagents include, but are not limited to, silver nitrate, silver acetate, silver citrate, osmium tetroxide, diaminobenzidine, tetrazolium dyes, peroxidase reaction product of 3,3',5,5'-Tetramethylbenzidine (17 MB), alkaline phosphatase reaction product of BLIP or any other indigo-containing product (e.g. :3-IP or any of the other substituted indoxyl phosphates). In another embodiment, the substrate entity produces a product that enhances the color of metallic nanoparticles. The product may be formed enzymatically. For instance, in one embodiment, the detectable entity is a metallic nanoparticle conjugated to an enzyme and the substrate entity is a substrate of the enzyme. In some embodiments, the detectable entity is a gold nanoparticle-enzyme conjugate and the substrate entity is 3,3',5,5'-Tetramethylbenzidine (FMB) or an indigo-containing product (e.g. BCIP or 3-IP).

The substrate region can comprise one or more additional reagents that act to slow the flow of fluid through the second flow path. In one embodiment, the substrate region comprises one or more slowly dissolving polymers (e.g. dissolution retardants); such as polyvinylpyrrolidone, polyvinyl alcohol, polyethylene glycol, ethylceilutose, hydroxypropylmethylcellulose, Eudragit® and equivalent polymethacrylate products, hydroxypropyiethyicellulose and hydroxypropyicenulose, or various guar gums, to retard the dissolution of dried substrate or amplifying reagent present in the substrate region, thus prolonging the delivery of the substrate or amplifying reagent to the capture ligand located in the first flow path. In some embodiments, higher molecular weight polyvinylpyrrolidortes are preferred. In still another embodiment, the substrate region is gelled with calcium-alginate and is fluidized with EGTA contained in the sample port.

In certain embodiments, the second flow path is in fluid communication with the sample port of the detection system such that liquid sample flows into both the first and second flow paths when centrifugal force is applied to the system. In other embodiments, the second flow path comprises a sample entry region positioned downstream of the sample port and upstream of the substrate entry region. The sample entry region can be in fluid communication with the first flow path. In such embodiments, when centrifugal force is applied to the system, fluid sample deposited in the sample port enters the first flow path and subsequently enters the second flow path through the sample entry region. In some embodiments, the second flow path further comprises a substrate entry region positioned downstream of the substrate region. The substrate entry region can also be in fluid communication with the first flow path. In certain embodiments, fluid communication between the substrate entry region and the first flow path is established through a semi-permeable membrane or an air gap that fills upon liquid absorption. Preferably, fluid from the second How path re-enters the first How path upstream of the capture ligand through the substrate entry region.

Thus, in certain embodiments in which each channel of the detection system of the invention comprises a first and second flow path, a centrifugal force applied to the system will cause liquid sample deposited in the sample port of the system to flow radially into the first and second flow paths of each channel. Fluid and dissolved reagents, such as enzyme substrates and amplifying reagents, from the second flow path will be delivered to the immobilized capture ligands located in the first flow path at a later point in time than fluid in the first flow path. For instance, in one embodiment, when a centrifugal force is applied to the detection system, liquid sample placed in the sample port will flow radially into the first and second flow paths of each channel Liquid sample entering the first flow path will contact the conjugate and any target analyte present in the sample will form a complex with the conjugate. The fluid will continue to flow downstream through the first flow path to the immobilized capture ligand, where the target analyte-conjugate complex will bind to the capture ligand. The fluid sample entering the second flow path will contact and solubilize the substrate entity (e.g. enzyme substrate or amplifying reagent) in the substrate region and flow downstream re-entering the first flow path through the substrate entry region. The dissolved substrate entity will then contact the capture ligand and any bound target analyte-conjugate complex producing a detectable signal or enhancing a detectable signal. The flow rates through the first and second flow paths of each channel can be controlled by applying different strength centrifugal forces. For example, in one embodiment, a lower strength centrifugal force will cause liquid sample to flow through the first flow path to the capture ligand, while a higher strength centrifugal force will result in the flow of fluid through the second flow path, which is delayed due to the presence of viscous materials or valves that preferentially open at higher speeds.

In one embodiment, the surface comprises a plurality of channels (e.g. two or more), wherein each channel comprises a conjugate capable of binding to an analyte in the sample to form a complex and wherein the complex is captured by a capture ligand. In certain embodiments, each conjugate is capable of binding to a different analyte in the sample such that multiple analytes can be detected simultaneously. The detectable entities in each conjugate can be the same or different. For instance, the detectable entities in each conjugate may be a gold nanoparticle. Alternatively, the detectable entity in a first conjugate may be a gold nanoparticle, while the detectable entity in a second conjugate may be a silver nanoparticle. In some embodiments, all the detectable entities in a single detection system are of the same type (e.g. metal nanoparticles/nanoshells, fluorescent molecules, colored latex particles, or enzymes).

In another embodiment, the sample port comprises at least one conjugate capable of binding to an analyte in the sample to form a complex, wherein the complex is captured by a capture ligand downstream of the sample port. In certain embodiments, the sample port comprises two or more conjugates capable of binding a target analyte. In preferred embodiments, each conjugate is capable of binding a different target analyte in the sample. The detectable entities in each of the conjugates can be the same or different.

Conjugates can be deposited directly on the surface or channel material or can be deposited on a porous material, which in turn is affixed to the surface or channel material. Porous materials on which conjugates are deposited may further comprise one or more excipients to stabilize the conjugates. Such excipients will depend on the type of binding partner and detectable entity that comprise the conjugate, but can include albumins, caseins, gelatin, polymeric stabilizers such as polyvinylpyrrolidone or polyvinyl alcohol, or sugars like sucrose and trehalose. In some embodiments, the conjugates are lyophilized or dried and are solubilized upon contact with the sample during operation of the detection system.

In another embodiment of the invention, the one or more channels present on the surface further contain a positive or negative control entity. The control entity can operate as a positive control for the detection system. For instance, a detectable signal from the control entity can indicate that the liquid sample applied to the detection system has reached the capture ligand(s) of the system (e.g. the fluidics of the radial flow paths are functioning properly). This function of the control entity helps to eliminate false negatives due to improper flow of the sample through the detection system. In some embodiments, the control entity is an immobilized control binding partner. In one embodiment, the control binding partner is capable of specifically binding to the unreacted conjugate (e.g. the binding partner or detectable entity). By way of example, the control binding partner can be an anti-body that specifically binds to the binding partner or detectable entity. Preferably, the detection signal is the same for both the conjugate and control.

In another embodiment, the control binding partner is capable of specifically binding to an artificial component (e.g. control conjugate) that has been added to the sample. The artificially added control conjugate can be supplied to the sample prior to sample application to the detection system or it may be dried onto a porous material located in the sample port of the system. For instance, biotin coupled to a detectable entity (e.g. biotin conjugate) can be supplied to the sample. In this case, the control binding partner can be streptavidin, which would bind the artificially added biotin conjugate. In preferred embodiments, the detectable entity coupled to the artificially added substance is the same as the detectable entity in the conjugate.

In one embodiment, the positive or negative control entity is positioned in each channel downstream of each capture ligand. See, e.g., FIG. 1. In such an embodiment, the control entity indicates proper fluid flow in each radial flow path or channel. In another embodiment, the positive or negative control entity is positioned at the end of a single flow path downstream of all capture ligands. See, e.g., FIG. 2. In this embodiment, the control entity indicates whether the sample was transported along the full-length of the flow path to the end of the detection system. Control entities can be immobilized to surface, channel, or porous materials with methods similar to those described herein for immobilizing capture ligands.

In some embodiments, the surface further contains at least one absorbing entity located downstream of the capture ligand. The absorbing entity can be positioned at the end of a single flow path downstream of one or more capture ligands FIG. 2). In another embodiment, two or more absorbing entities are positioned on the surface so as to separate two or more flow paths (e.g., FIG. 1). For instance, a first absorbing entity can be positioned at the end of a first radial flow path downstream of a first capture ligand and a second absorbing entity can be positioned at the end of a second radial flow path downstream of a second capture ligand such that the first and second radial flow paths do not intermix. The one or more absorbing entities can supplement the function of the centrifugal force in moving fluids through the one or more radial flow paths of the detection system. The absorbing entities also function to remove excess fluid from other components of the system and can help pull away unreacted (e.g. uncaptured) conjugate, thus preventing an undesirable background noise at the capture ligands. The absorbing entity can be constructed from cellulose materials or the like or can be a hygroscopic powder, polymer, or material. In a preferred embodiment, the absorbing entity is a cross linked polyacrylamide copolymer that absorbs water (e.g., Waterlock®).

The detection system of the invention is preferably adapted for use with a centrifugal force. In one embodiment, the centrifugal force is operably connected to the sample port so that when in operation it causes a sample deposited in the sample port to move through the one or more channels present on the surface and be in fluid contact with the one or more capture ligands. As used herein "operably connected" means that the centrifugal force is applied to the sample port such that the sample port and surface rotate about a fixed axis (e.g. vertical or horizontal axis). The centrifugal force causes a fluid sample deposited in the sample port to flow radially outward along channels to the periphery of the surface. The centrifugal force-driven movement allows the sample to interact with reagents and capture ligands deposited at various points along the flow paths. In embodiments in which each channel comprises a first and second flow path (i.e. dual flow paths), the applied centrifugal force causes the fluid sample to flow into both flow paths. In some embodiments, a higher centrifugal force is required to move fluid through the second flow path of each channel as compared to the centrifugal force required to move fluid through the first flow path of each channel. In one embodiment, two different centrifugal forces are applied to the detection system at different times. For instance, a lower centrifugal force (i.e. low speed spin) is applied to the system to move liquid sample from the sample port into the first flow path of each channel to the capture ligands located on the peripheral edge of the surface. A second, higher centrifugal force (i.e. high speed spin) is subsequently applied to the system to move the sample through the second flow path of each channel to contact the capture ligands located on the peripheral edge of the surface. Thus, the delivery of reagents to the capture ligands of the detection system can be delayed by employing a second flow path in each channel.

The applied centrifugal force can be from about 500 g to about 2,000 g, from about 800 g to about 1,600 g, or from about 1,000 g to about 1,200 g. The detection system can be used with conventional centrifuges as long as the appropriate centrifugal forces can be applied. In some embodiments, the detection system is adapted for use with the Piccolo® xpress and VetScan® analyzers available from Abaxis, (Union City, Calif.).

One embodiment of the analyte detection system of the invention is illustrated in FIG. 1. In this embodiment, the detection system comprises a surface, such as a rotor base or disc, containing a plurality of channels that are in fluid communication with a sample port. Each channel contains a conjugate comprised of a binding partner conjugated to a detectable entity that can specifically bind to a target analyte present in the sample. At the peripheral edge of each channel is a capture ligand capable of binding the analyte-conjugate complex. The peripheral edge can optionally contain a control entity (control tine) that indicates sufficient fluid flow through the system. The sample port may optionally contain a blood separator material when the detection system is used to analyze whole blood samples.

A liquid sample containing one or more analytes is deposited. In the sample port. A centrifugal force is applied to the surface and sample port such that the surface and sample port spin about a fixed axis. The fluid sample in the sample port flows radially outward through the channels to the periphery of the surface (blue arrows). The sample flowing through each radial flow path will pass through the conjugate where it will solubilize the dried conjugate. If the target analyte is present in the sample, the conjugate will bind to the target analyte forming a complex and continue to flow downstream to the capture ligand. The immobilized capture ligand present at the peripheral edge of the surface will bind to and capture the target analyte-conjugate complex. Excess fluid containing unreacted conjugate (e.g. not bound to the target analyte) will pass through the region containing the capture ligand and into the region containing the control entity (if present), which will capture some of the unreacted conjugate. The remaining sample will be absorbed by one or more absorbing entities positioned downstream of each capture ligand. The conjugates and capture ligands in each radial flow path (channel) can bind to a different analyte in the sample, thereby allowing simultaneous detection of multiple analytes. A detectable signal measured from each captured analyte-conjugate complex at the peripheral edge of each channel indicates that the particular analyte is present in the sample.

Figure 2:
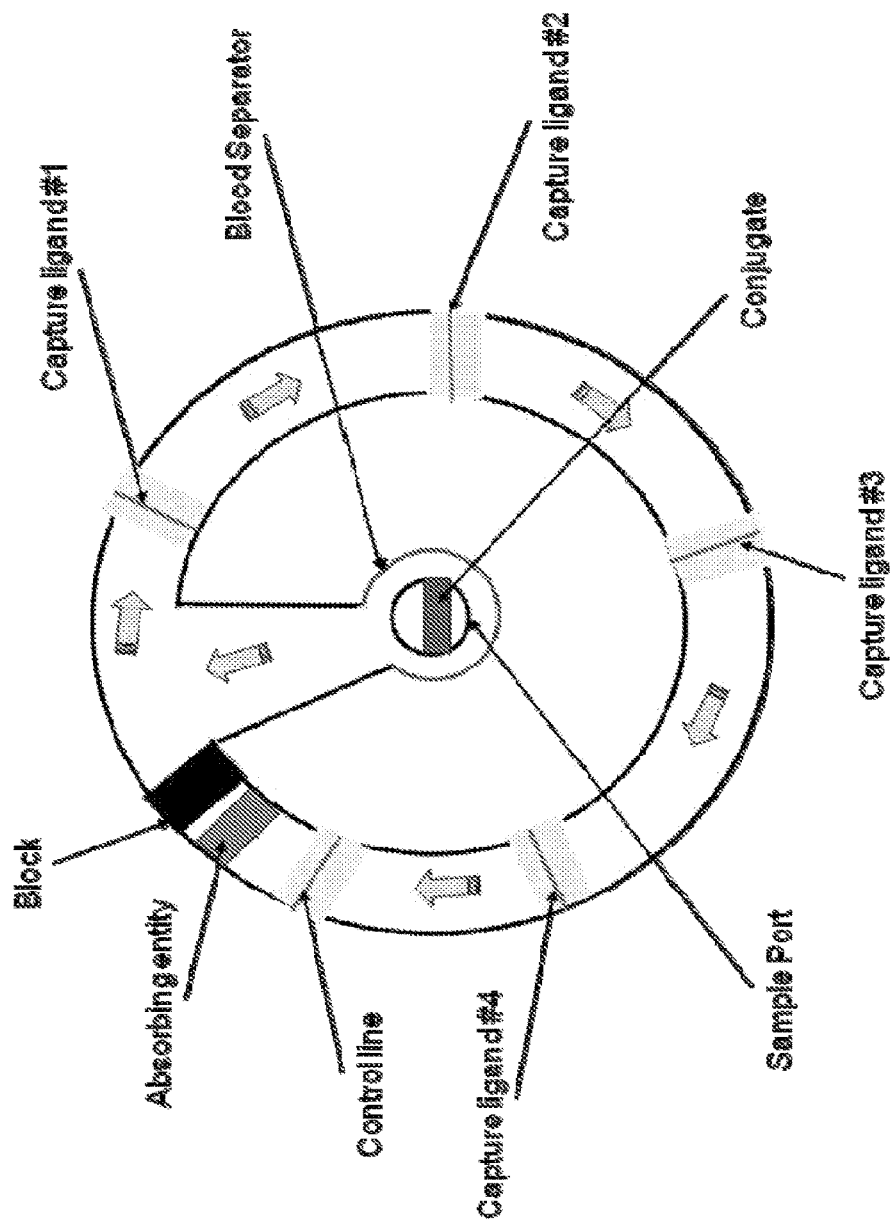
FIG. 2 illustrates a top view of another embodiment of the analyte detection system of the present invention. A surface (e.g. rotor base or disc) contains a single channel in fluid communication with a sample port. The sample port contains multiple conjugates, each of which is comprised of a binding partner conjugated to a detectable entity. The conjugates are capable of specifically binding to different target analytes present in the sample. The peripheral edge of the surface contains multiple capture ligands capable of binding particular analyte-conjugate complexes. When a centrifugal force is applied to the surface, a fluid sample deposited in the sample port contacts the multiple conjugates. If the particular analyte to which the conjugate binds is present in the sample, an analyte-conjugate complex is formed and flows radially through the channel to the periphery of the surface (blue arrows). Capture ligand immobilized on the peripheral edge of the surface will capture the analyte conjugate complex. Multiple analytes in the sample may be detected by employing different capture ligands that specifically bind to the different analyte-conjugate complexes. Excess fluid is absorbed by absorbent material (absorbing entity) positioned at the end of the peripheral flow path (e.g., downstream of all capture ligands). A control line, which indicates sufficient fluid flow through the system, may optionally be positioned at the end of the peripheral flow path upstream of the absorbing entity. Preferably, a water impervious material (block) is positioned between the end of the peripheral flow path and the point where the channel delivers fluid to the peripheral edge of the surface. The surface can optionally contain a blood separator material, which allows plasma from a blood sample to pass into the system while retaining cellular material in the sample port.

FIG. 2 illustrates another embodiment of the analyte detection system of the invention. In this embodiment, the detection system comprises a surface (e.g. rotor base or disc) containing a single channel fluid communication with a sample port. The sample port contains multiple conjugates, each of which are comprised of a binding partner conjugated to a detectable entity. The conjugates are capable of specifically binding to different target analytes present in the sample. The peripheral edge of the surface contains multiple capture ligands capable of binding particular analyte-conjugate complexes. A control entity (control line), which indicates sufficient fluid flow through the system, may optionally be positioned at the end of the peripheral flow path upstream of the absorbing entity. Preferably, a water impervious material (block) is positioned between the end of the peripheral flow path and the point where the channel delivers fluid to the peripheral edge of the surface. The block or dam can be constructed from plastic, silica plate, metal plate, or a laminated or coated material or other water impervious material. When the detection system is used for analyzing whole blood samples, the sample port can optionally contain a blood separator material, which allows plasma from a blood sample to pass into the system while retaining cellular material in the sample port.

In this format, a sample containing one or more target analytes is deposited in the sample port, which solubilizes and interacts with the multiple conjugates. If the particular analytes to which each of the conjugates bind is present in the sample, analyte-conjugate complexes are formed. A centrifugal force is applied to the sample port and surface such that the surface and sample port spin about a fixed axis. The sample fluid containing the analyte-conjugate complexes flows radially through the channel to the periphery of the surface (blue arrows). Capture ligands immobilized on the peripheral edge of the surface will sequentially capture each of the analyte-conjugate complexes, Excess fluid sample is absorbed by an absorbing entity positioned at the end of the peripheral flow path (e.g., downstream of all capture ligands). A detectable signal measured from each captured analyte-conjugate complex at each of the peripheral sets of capture ligand indicates that the particular analytes are present in the sample.

The present invention also includes kits comprising the analyte detection systems of the invention as disclosed herein. In one embodiment, the kit comprises an analyte detection system and instructions for using the system to detect one or more analytes in a test sample, wherein the detection system is adapted for use with a centrifugal force and comprises a sample port and a surface, said surface containing at least one channel, said channel comprising an immobilized capture ligand capable of specifically binding to an analyte in a sample, and wherein the sample port is in fluid communication with said at least one channel In certain embodiments, the surface is in a rotor or disc format capable of use with conventional centrifuges. The kit can further include means for collecting biological samples or extraction buffers for obtaining samples from solid materials, such as soil, food, and biological tissues.

The present invention also encompasses a method for detecting an analyte in a sample. In one embodiment, the method comprises adding the sample to the sample port of a detection system disclosed herein, applying a centrifugal force to the system, and detecting the binding of the analyte to the capture ligand. In some embodiments, the detection step comprises measuring an optical signal from a captured analyte-conjugate complex. The invention provides a method for detecting multiple analytes present in a single sample simultaneously. The methods can provide qualitative and or quantitative analysis of the detected analytes.

A sample can be any type of liquid sample, including biological samples or extracts prepared from environmental or food samples. In a preferred embodiment, the sample is a biological sample. Biological samples include, but are not limited to, whole blood, plasma, serum, urine, pleural effusion, sweat, bile, cerebrospinal fluid, fecal material, vaginal fluids, sperm, ocular lens fluid, mucous, synovial fluid, peritoneal fluid, amniotic fluid, biopsy tissues, saliva, and cellular lysates. The biological sample can be obtained from a human subject or animal subject suspected of having a disease condition, such as cancer, infectious diseases (e.g., viral, bacterial, parasitic or fungal infections), cardiovascular disease, autoimmune etc. The biological sample can also be obtained from a healthy subject (e.g. human or animal) undergoing a routine medical check-up.

Any type of target analyte can be detected using the methods and systems of the present invention. An "analyte" refers to any substance capable of being bound by a capture ligand or binding partner of the conjugates disclosed herein. An analyte encompasses derivatives or metabolites of the compound of interest. In some embodiments, the analytes are associated with infectious diseases in both humans and animals. In other embodiments, the analytes are markers of a particular physiological or pathological condition. A target analyte can be a protein, peptide, nucleic acid, hapten, or chemical.

In certain embodiments, the analyte is a pathogenic antigen or antibody to a pathogenic antigen, For instance, the pathogenic antigen can be a viral antigen (e.g., feline leukemia virus, canine parvovirus, foot and mouth virus, influenza virus, hepatitis a, b, c virus, HIV virus, human papilloma virus, epstem barr virus, rabies virus, etc.), a bacterial antigen (e.g., *Ehrlichia*, Borellia, Anthrax, *Salmonella, Bacillus,* etc.), a fungal antigen, or parasitic antigen (e.g., canine heart-worm, *Giardia lamblia, plasmodium falciparum,* african try-panosomiasis, *trypanosoma brucei,* etc.). In other embodiments, the artalyte is a disease-related antigen or antibody to a disease-related antigen. Disease-related antigens include, but are not limited to, cancer-related antigens (e.g., PSA, AFP, CA125, CA15-3, CA19-9, CEA, NY-ESO-1. MUC1, GM3, GD2, ERBB2, etc.), cardiovascular disease-related antigens (e.g., troponin, CRP, CKMB, fatty acid binding protein, etc.), or autoimmune disease-related antigens (e, auto-antibodies). In certain embodiments, the analyte is a inflammatory antigen (e.g., C-reactive protein, MRP14, MRP8, 25F9, etc.). In other embodiments, the analyte is a pregnancy-related antigen (e.g., a fetal antigen).

Detection of binding of the analyte to the capture ligand comprises observing or measuring the signal from the detectable entity of captured analyte-conjugate complexes. in some embodiments, the signal is a spectral shift (e.g. color change). In other embodiments, the signalis a fluorescent signal. The detection signal corresponding to the presence of any captured analyte-conjugate complexes at the capture ligands can be detected visually or by means of an instrument. In one embodiment, the signal is detected by measuring a change in absorbance of the signal. Commercial instruments capable of detecting spectral shifts or changes in fluorescence can be used to measure the detection signal from captured analyte-conjugate complexes of the detection systems. Such instruments include "strip readers" and are known to those skilled in the art. The means for detecting a signal from the detectable entity in the captured analyte-conjugate complexes can be located in the same instrument that applies the centrifugal force. Quantitative analysis of the analytes can be achieved by measuring spectral shifts or absorbance changes and comparing the shifts/changes to those obtained with known concentrations of analytes. For instance, in one embodiment, concentration of the target analyte in a sample can be calculated from the intensity of the optical signal (e.g. intensity of color change) at the capture ligand. Detection of a signal from the control entity of the analyte detection systems of the invention is indicative of proper fluid flow through the device. Detection of a signal from the regions containing capture ligands of the analyte detection systems of the invention is indicative of the presence of target analyte in the sample (e.g. positive sample). Similarly, absence of a signal-from the regions containing capture ligands of the analyte detection systems of the invention is indicative of the absence of target analyte in the sample (e.g. negative sample).

It is understood that the disclosed invention is not limited to the particular methodology, protocols and materials described as these can vary. It is also understood that the terminology used herein is for the purposes of describing particular embodiments only and is not intended to limit the scope of the present invention which will he limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for detecting an analyte in a sample comprising
   (i) adding the sample to a sample port of a device, the device comprising the sample port and a surface, wherein the surface comprises a single channel in fluid communication with the sample port and a circular flow path at the peripheral edge of the surface, wherein the sample port and/or the channel comprises a conjugate comprising a binding partner that can specifically bind to the analyte, and wherein the circular flow path comprises an immobilized capture ligand capable of binding an analyte-conjugate complex;
   (ii) spinning the surface and the sample port about a fixed axis to generate a centrifugal force, wherein the centrifugal force causes the sample added to the sample port to flow through the channel and come into fluid contact with the capture ligand; and
   (iii) detecting the binding of the analyte in the sample to the capture ligand.

2. The method of claim 1, wherein the sample port and/or channel comprises a plurality of conjugates.

3. The method of claim 1, wherein the circular flow path comprises a plurality of capture ligands.

4. The method of claim 1, wherein the binding partner is conjugated to a detectable entity.

5. The method of claim 4, wherein the detectable entity is a metallic nanoparticle or metallic nanoshell.

6. The method of claim 4, wherein the detectable entity is selected from the group consisting of gold nanoparticles, silver nanoparticles, copper nanoparticles, platinum nanoparticles, cadmium nanoparticles, composite nanoparticles, gold hollow spheres, gold-coated silica nanoshells, and silica-coated gold shells.

7. The method of claim 4, wherein the detectable entity is an enzyme.

8. The method of claim 7, wherein the enzyme is selected from the group consisting of alkaline phosphatase, horseradish peroxidase, beta-galactosidase, beta-lactamase, luciferase, myeloperoxidase, and amylase.

9. The method of claim 1, wherein the surface further comprises at least one absorbing entity located downstream from the capture ligand.

10. The method of claim 2, wherein the plurality of conjugates comprises at least a first conjugate capable of binding a first analyte and a second conjugate capable of binding a second analyte, wherein the first and second analytes are different.

11. The method of claim 2, wherein each conjugate in the plurality of conjugates is capable of binding a different analyte.

12. The method of claim 2, wherein the plurality of conjugates comprise binding partners conjugated to different detectable entities.

13. The method of claim 3, wherein each of said plurality of immobilized capture ligands specifically binds to a different analyte-conjugate complex.

14. The method of claim 3, wherein each of said plurality of immobilized capture ligands are capable of specifically binding to the same analyte-conjugate complex.

15. The method of claim 14, wherein the immobilized capture ligands are immobilized at different concentrations.

16. The method of claim 3, wherein the plurality of capture ligands are arranged sequentially along the circular path.

17. The method of claim 1, wherein the sample port comprises a blood separator material that allows plasma from a blood sample to pass into the channel, while retaining cellular material from the blood sample in the sample port.

* * * * *

UNITED STATES PATENT AND TRADEMARK OFFICE
CERTIFICATE OF CORRECTION

| | |
|---|---|
| PATENT NO. | : 10,969,385 B2 |
| APPLICATION NO. | : 16/450082 |
| DATED | : April 6, 2021 |
| INVENTOR(S) | : Mehra et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this
Seventh Day of February, 2023

Katherine Kelly Vidal
*Director of the United States Patent and Trademark Office*